(12) United States Patent
Dente et al.

(10) Patent No.: US 9,114,180 B2
(45) Date of Patent: Aug. 25, 2015

(54) MALODOR NEUTRALIZING COMPOSITIONS CONTAINING ACIDS AND ALICYCLIC KETONES

(71) Applicant: Robertet, Inc., Oakland, NJ (US)

(72) Inventors: Stephen V. Dente, Oakland, NJ (US); Garry Johnson, Oakland, NJ (US); Ketrin Leka Basile, Oakland, NJ (US); Inga Verbicka-Rozitis, Oakland, NJ (US); Emily Belthoff, Oakland, NJ (US)

(73) Assignee: Robertet, Inc., Mount Olive, NJ (US)

( * ) Notice: Subject to any disclaimer, the term of this patent is extended or adjusted under 35 U.S.C. 154(b) by 127 days.

(21) Appl. No.: 13/829,487

(22) Filed: Mar. 14, 2013

(65) Prior Publication Data

US 2013/0259822 A1 Oct. 3, 2013

Related U.S. Application Data

(60) Provisional application No. 61/617,749, filed on Mar. 30, 2012.

(51) Int. Cl.
| | |
|---|---|
| *A61L 9/01* | (2006.01) |
| *A61Q 13/00* | (2006.01) |
| *C11B 9/00* | (2006.01) |
| *C11D 3/00* | (2006.01) |
| *C11D 3/50* | (2006.01) |
| *C11D 3/20* | (2006.01) |
| *C11D 7/26* | (2006.01) |
| *A61K 8/35* | (2006.01) |

(52) U.S. Cl.
CPC ... *A61L 9/01* (2013.01); *A61K 8/35* (2013.01); *A61Q 13/00* (2013.01); *C11B 9/0034* (2013.01); *C11D 3/0068* (2013.01); *C11D 3/2079* (2013.01); *C11D 3/2086* (2013.01); *C11D 3/50* (2013.01); *C11D 7/265* (2013.01)

(58) Field of Classification Search
CPC .... A61Q 13/00; C11B 9/0034; C11D 3/0068; A61K 8/35
USPC ........................................................ 424/76.1
See application file for complete search history.

(56) References Cited

U.S. PATENT DOCUMENTS

| | | |
|---|---|---|
| 4,000,329 A | 12/1976 | Pittet et al. |
| 4,009,253 A | 2/1977 | Schleppnik et al. |
| 4,010,253 A | 3/1977 | Reese et al. |
| 4,107,289 A | 8/1978 | Kaufman |
| 4,310,152 A | 1/1982 | Mitzel |
| 5,089,258 A | 2/1992 | Zaid |
| 5,098,694 A | 3/1992 | Komp et al. |
| 5,198,144 A | 3/1993 | Ichii et al. |
| 5,202,124 A | 4/1993 | Williams et al. |
| 5,451,346 A | 9/1995 | Amou et al. |
| 5,554,588 A | 9/1996 | Behan et al. |
| 5,589,164 A | 12/1996 | Cox et al. |
| 5,662,937 A | 9/1997 | McCuaig |
| 5,676,163 A | 10/1997 | Behan et al. |
| 5,720,947 A | 2/1998 | Basset et al. |
| 5,795,566 A | 8/1998 | Joulain et al. |
| 5,800,897 A | 9/1998 | Sharma et al. |
| 6,019,855 A | 2/2000 | Finch et al. |
| 6,495,097 B1 | 12/2002 | Streit et al. |
| 6,753,308 B1 | 6/2004 | Richardson et al. |
| 6,906,045 B2 | 6/2005 | Ebube et al. |
| 7,147,822 B2 | 12/2006 | Parkhurst et al. |
| 7,157,411 B2 | 1/2007 | Rohde et al. |
| 7,261,742 B2 | 8/2007 | Leskowicz |
| 7,407,515 B2 | 8/2008 | Leskowicz |
| 7,407,922 B2 | 8/2008 | Leskowicz |
| 7,569,232 B2 | 8/2009 | Man et al. |
| 7,638,118 B2 | 12/2009 | Flachsmann et al. |
| 8,323,256 B2 * | 12/2012 | Edgett et al. ............. 604/385.18 |
| 2002/0197287 A1 | 12/2002 | Streit et al. |
| 2003/0113289 A1 | 6/2003 | Hu et al. |
| 2004/0091595 A1 | 5/2004 | Dewis et al. |
| 2004/0221858 A1 | 11/2004 | Higashi et al. |
| 2006/0228250 A1 | 10/2006 | Brown et al. |
| 2006/0287219 A1 | 12/2006 | Dykstra et al. |
| 2007/0054815 A1 | 3/2007 | Convents et al. |
| 2007/0231278 A1 | 10/2007 | Lee et al. |
| 2008/0207481 A1 | 8/2008 | Meine et al. |
| 2008/0221003 A1 | 9/2008 | Meine et al. |
| 2010/0021413 A1 | 1/2010 | McGee et al. |
| 2010/0028288 A1 | 2/2010 | Tranzeat et al. |

(Continued)

FOREIGN PATENT DOCUMENTS

| | | |
|---|---|---|
| AU | 2009101152 | 1/2010 |
| DE | 3045483 A1 | 12/1982 |

(Continued)

OTHER PUBLICATIONS

International Search Report and Written Opinion mailed on Nov. 14, 2013 in International Application No. PCT/US2013/033927.
International Search Report dated Aug. 19, 2013 issued in corresponding PCT Application No. PCT/US2013/033927.
Matsubara, E., et al., "(−)-Bornyl acetate induces autonomic relaxation and reduces arousal level after visual display terminal work without any influences of task performance in low-dose condition," *Biomed Res* Apr. 2011; 32(2):151-7 (Abst).
International Preliminary Report on Patentability mailed in corresponding International Application No. PCT/US2011/022697 on Dec. 13, 2012.

(Continued)

*Primary Examiner* — Johann R Richter
*Assistant Examiner* — Yanzhi Zhang
(74) *Attorney, Agent, or Firm* — Fish & Richardson P.C.

(57) ABSTRACT

This disclosure relates to a malodor neutralizing composition containing (1) a cyclohexanone substituted with $C_1$-$C_5$ branched or unbranched alkyl or an unsaturated alicyclic ketone of formula (I) and (2) an acid selected from the group consisting of citric acid, undecylenic acid, and an acid of the formula (VIII). Formulas (I) and (VIII) are defined in the specification.

19 Claims, No Drawings

(56) References Cited

U.S. PATENT DOCUMENTS

| | | |
|---|---|---|
| 2010/0034766 A1 | 2/2010 | McGee et al. |
| 2010/0111889 A1* | 5/2010 | Marsh et al. ............ 424/76.1 |
| 2011/0239736 A1 | 10/2011 | Ramji et al. |
| 2011/0305659 A1 | 12/2011 | Woo et al. |

FOREIGN PATENT DOCUMENTS

| | | |
|---|---|---|
| GB | 801726 A | 9/1958 |
| GB | 1311060 | 3/1973 |
| GB | 2187642 | 9/1987 |
| JP | 63-066115 | 3/1988 |
| JP | 7-291809 | 11/1995 |
| JP | 2000-282081 A | 10/2000 |
| WO | WO 97/15283 | 5/1997 |
| WO | WO 98/56889 | 12/1998 |
| WO | WO 00/27442 | 5/2000 |
| WO | WO 00/72890 | 12/2000 |
| WO | WO 03/051410 | 6/2003 |
| WO | WO 2006/102052 | 9/2006 |
| WO | WO 2006/131739 | 12/2006 |
| WO | WO 2011/152886 | 12/2011 |

OTHER PUBLICATIONS

International Search Report and Written Opinion mailed in corresponding International Application No. PCT/US2012/022209 on Apr. 4, 2012.

International Search Report and Written Opinion mailed in corresponding International Application No. PCT/US2011/022697 on Jul. 5, 2012.

International Preliminary Report on Patentability mailed in corresponding International Application No. PCT/US2012/022209 on Aug. 8, 2013.

* cited by examiner

MALODOR NEUTRALIZING COMPOSITIONS CONTAINING ACIDS AND ALICYCLIC KETONES

CROSS-REFERENCE TO RELATED APPLICATION

This application claims priority to U.S. Provisional Application No. 61/617,749, filed on Mar. 30, 2012, the contents of which are hereby incorporated by reference in their entirety.

TECHNICAL FIELD

This disclosure relates to odor neutralizer compositions and their use for reducing malodors.

BACKGROUND

In many application areas, perfumes are used for masking malodors. Annoyance caused by malodors occurs frequently in daily life and impairs personal well-being. Such malodors are, for example: those resulting from substances transpired or excreted by humans, in particular, perspiration, mouth odors, feces and urine; odors caused by animal feces or urine, in particular, those of domestic pets; kitchen odors, such as those resulting from the preparation of onions, garlic, cabbage or fish; and odors due to tobacco smoke, garbage, bathrooms, molds and waste.

In addition, malodors may be caused by many industrially produced basic materials used in cleansing agents, such as, for example, detergents and fabric softeners, or in body care products, such as, for example, soaps and cosmetics. The use of specific cosmetic preparations, such as, for example, hair dyes, and depilatories, also produces malodors.

Many rubber and plastic products also produce malodors if, due to the method of their manufacture, they still contain quantities of highly odorous, volatile active ingredients. These malodors are usually caused by particularly odorous substances which are, however, generally only present in trace amounts. Such substances include, for example, nitrogen-containing compounds such as ammonia and amines, heterocyclic compounds such as pyridines, pyrazines, indoles, etc., and sulfur-containing compounds such as hydrogen sulfide, mercaptans, sulfides, etc.

The masking of malodors is a problem which is difficult to handle and solve with perfume compositions. Usually, it is only possible to mask malodors by means of a specially developed perfume oil having specific types of fragrances.

Malodor counteracting compositions are particularly advantageous when they are capable of reducing the intensity of malodors without themselves possessing any significantly intense odor or fragrance. Such active ingredients do not mask malodors; rather, they neutralize the malodors. This has the advantage that, when using such active ingredients for perfuming objects or products having malodors, perfume oils of any desired type of fragrance can be used. The consumer can, therefore, be offered a considerably broader range of fragrance types for combating malodors.

In addition, active ingredients which neutralize malodors, provide the possibility of reducing the quantity of perfume oil previously required for masking odors. It is also possible to use less intensely odorous perfumes for combating malodors than those heretofore employed.

Another area in which malodor reducing compositions find utility is in breath freshening compositions such as chewing gum, mints, mouthwashes, lozenges and sprays. In addition to flavoring and perfuming ingredients which mask oral malodors, it is also useful to neutralize the ingredients which cause such malodors.

In recent years, a wide variety of substances have been proposed for use in neutralizing malodors, including some substances traditionally used as perfumes and/or as ingredients in deodorizing compositions. Unsaturated alicyclic ketone derivatives such as ionones, irones, damascones and damascenones are well-known perfuming ingredients and have been used as perfuming agents and masking deodorants in a wide variety of consumer products. Recently, these alicyclic ketones have been used in combination with other fragrancing, odor neutralizing and biocidal substances.

U.S. Pat. No. 7,651,994 discloses the use of ionones, irones and damascone in combination with decamethyltetrasiloxane. U.S. Pat. No. 7,776,811 discloses cleaning compositions comprising damascones, ionones and/or damascenones in combination with certain betaines and biocides. U.S. Pat. No. 8,058,224 discloses the use of certain ionones and irones as perfuming ingredients in fabric conditioning compositions. U.S. Pat. No. 8,076,519 discloses the use of ionones, irones, damascones and damascenone as odor-masking agents in sulfur-containing compositions. U.S. Patent Publication 2011/0104089 discloses certain ionones and damascones as components of compositions containing mixtures of fragrances. And U.S. Patent Publication 2011/0293668 discloses ionones and irones as odor control agents in oral care compositions.

SUMMARY

In general, this disclosure provides a malodor neutralizing composition comprising a combination of (1) a cyclohexanone substituted with $C_1$-$C_5$ branched or unbranched alkyl or an unsaturated alicyclic ketone of formula (I) (e.g., ionones, irones, damascones and damascenones) and (2) citric acid, undecylenic acid, or a monocarboxylic acid of the formula $$R—COOH \qquad (VIII)$$

in which R is $C_1$-$C_5$ alkyl or R is $C_3$ or $C_4$ alkylene optionally substituted by phenyl.

DETAILED DESCRIPTION

The alicyclic ketones have the general formula

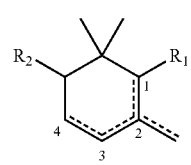

wherein
the ring contains 1 double bond at position 1, position 2 (endocyclic) or position 2 (exocyclic) or contains 2 conjugated double bonds at positions 1 and 3,
$R_1$ is a branched or unbranched $C_3$-$C_5$ alkyl containing a carbonyl group or a branched or unbranched $C_3$-$C_5$ alkenyl containing a carbonyl group, and
$R_2$ is hydrogen or methyl.

Preferred ketones within structure (I) are those in which $R_1$ is alkyl or alkylene having 4 or 5 carbon atoms with the carbonyl group being in the 1' or 3' position relative to the ring.

Particularity preferred are ketones in which $R_1$ is alkylene having 4 carbon atoms, such as

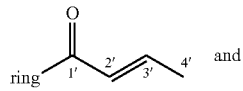

(II)

and

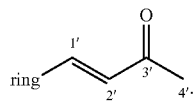

(III)

These alicyclic ketones include ionones of the general structure (IV):

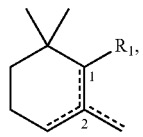

(IV)

in which, in $R_1$, the carbonyl group is in the 3' position as shown in structure (III). Ionones have three isomeric forms depending on location of the single double bond of the ring

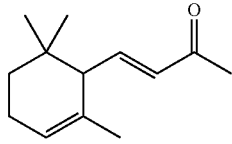

α-ionone
double bond in the 2-endo position

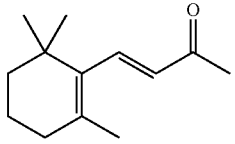

β-ionone
double bond in the 1 position

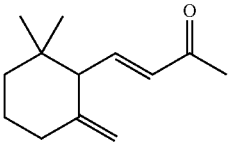

γ-ionone
double bond in the 2-exo position

In addition to ionone itself, there are other ionones falling within the general structure (IV) which include

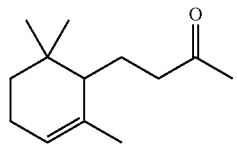

dihydro α-ionone

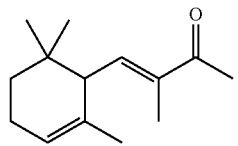

isomethyl α-ionone
(3-methyl-α-ionone)

and

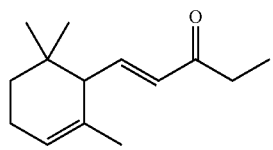

n-methyl α-ionone
(1-(2,6,6-trimethyl-2-cyclohexen-1-yl)pent-1-en-3-one)

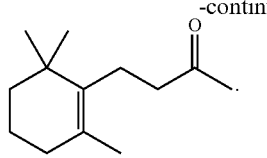

dihydro β-ionone

It should be understood that the just-mentioned α-isomers have corresponding β- and γ-isomers and the just-mentioned β-isomer has corresponding α- and γ-isomers.

The alicyclic ketones also include irones of the general structure (V):

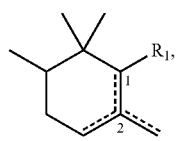

(V)

in which, in $R_1$, the carbonyl group is in the 3' position as shown in structure (III). As with the ionones, all of the irones exist in three isomeric forms, depending on location of the single double bond of the ring, such as:

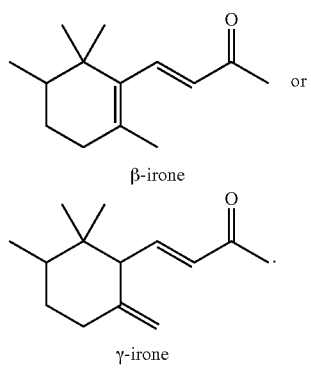

β-irone or

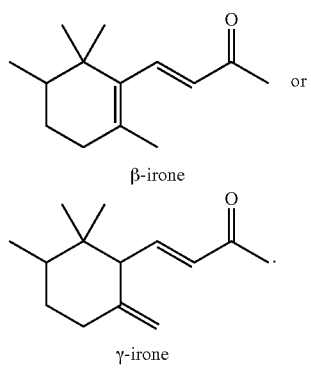

γ-irone

The just-mentioned β- and γ-irones have corresponding α-isomers.

In addition to irone itself, there are other compounds falling within the general structure (V) such as:

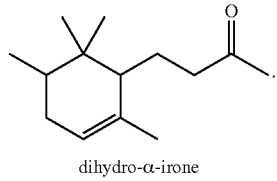

dihydro-α-irone

The alicyclic ketones include damascones of the general structure (VI).

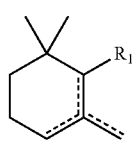

(VI)

in which, in $R_1$, the carbonyl group is in the 1' position as shown in structure (II). Like ionones and irones, all of the damascones exist in three isomeric forms depending on location of the double bond of the ring, such as:

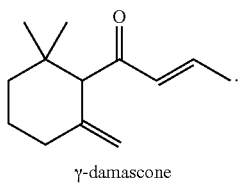

γ-damascone

There are corresponding α- and β-isomers.

The alicyclic ketones also include damascenones of the general structure (VII).

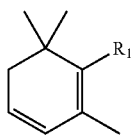

(VII)

in which, in $R_1$, the carbonyl group is in the 1' position as shown in structure (II).

Damascenone itself has the structure:

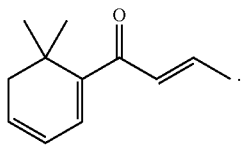

Further information about these alicyclic ketones may be found in David J. Rowe, "Chemistry and Technology of Flavor and Fragrances", sect. 4.6.1., Ed. 1, Nov. 12, 2004, incorporated herein by reference.

Another ketone which is usable in the compositions described in this disclosure is a substituted cyclohexanone (e.g., cyclohexanone substituted with $C_1$-$C_5$ branched or unbranched alkyl). Examples of such cyclohexanones include:

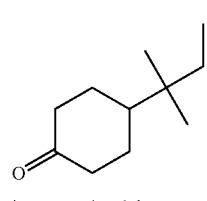

4-tert-penylcyclohexanone

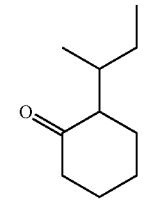

2-sec-butylcyclohexanone

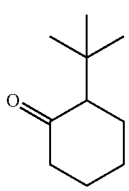

2-tert-butylcyclohexanone

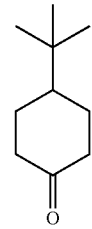

4-tert-butylcyclohexanone

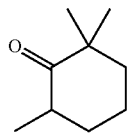

2,2,6-trimethylcyclohexanone

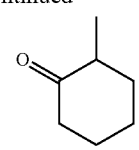

2-methylcyclohexanone

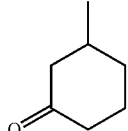

3-methylcyclohexanone

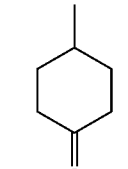

4-methylcyclohexanone.

The acids contained in the malodor neutralizing compositions invention described in this disclosure include citric acid

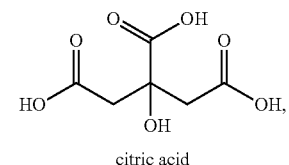 [SMILES: O=C(O)CC(O)(CC(=O)O)C(=O)O]

citric acid undecylenic acid

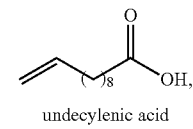

undecylenic acid and monocarboxylic acids of the general formula

R—COOH             (VIII), in which in R is $C_1$-$C_5$ alkyl or is a $C_3$ or $C_4$ alkylene optionally substituted by phenyl.

The preferred acids of structure (VIII) include acetic, propionic, butyric, valeric, isovaleric, caproic, hex-5-enoic, 2-methylbut-2-enoic (tiglic), and cinnamic acids.

In order to combat malodors, the combination of the one or more alicyclic ketones and one or more of these acids, are used in admixture. They may be used in pure form or in suitable solvents such as, for example, ethanol, isopropanol or other solvents well known for use in deodorizing formulations.

The ratio of alicyclic ketones to the acids can range from about 10% to 90%, preferably from about 25% to 75%. A weight ratio of about 50% is particularly preferred and convenient.

Preferred acids are citric, undecylenic, acetic, propionic, butyric, hex-5-enoic, tiglic, caproic and cinnamic acids.

In odor neutralizers, the compositions according to the present disclosure comprising one or more of the alicyclic ketones and one or more of these acids can be combined with one or more of a wide variety of fragrances.

The following may be mentioned as examples of ingredients used in fragrance compositions, in particular:

extracts from natural raw materials such as essential oils, resins, resinoids, balsams, tinctures such as for example ambergris tincture; amyris oil; angelica seed oil; angelica root oil; aniseed oil; valerian oil; basil oil; tree moss absolute; bay oil; armoise oil; benzoe resinoid; bergamot oil; beeswax absolute; birch tar oil; bitter almond oil; savory oil; buchu leaf oil; cabreuva oil; cade oil; calamus oil; camphor oil; cananga oil; cardamom oil; cascarilla oil; cassia oil; cassie absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; eau de brouts absolute; oakmoss absolute; elemi oil; estragon oil; eucalyptus citriodora oil; eucalyptus oil (cineole type); fennel oil; fir needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calamus oil; blue camomile oil; Roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil expressed; linaloe oil; Litsea cubeba oil; laurel leaf oil; mace oil; marjoram oil; mandarin oil; massoi (bark) oil; mimosa absolute; ambrette seed oil; musk tincture; clary sage oil; nutmeg oil; myrrh absolute; myrrh oil; myrtle oil; clove leaf oil; clove bud oil; neroli oil; olibanum absolute; olibanum oil; opopanax oil; orange flower absolute; orange oil; origanum oil; palmarosa oil; patchouli oil; perilla oil; Peru balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmatian sage oil; Spanish sage oil; sandalwood oil; celery seed oil: spikelavender oil; star anise oil; storax oil; tagetes oil; fir needle oil; tea tree oil; turpentine oil; thyme oil; Tolu balsam; tonka bean absolute; tuberose absolute; vanilla extract; violet leaf absolute; verbena oil; vetiver oil; juniperberry oil; wine lees oil; wormwood oil; wintergreen oil; ylang-ylang oil; hyssop oil; civet absolute; cinnamon leaf oil; cinnamon bark oil; and fractions thereof or ingredients isolated therefrom;

individual fragrance ingredients from the group comprising hydrocarbons, such as for example 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

aliphatic alcohols, such as for example hexanol; octanol; 3-octanol; 2,6-dimethyl-heptanol; 2-methyl-2-heptanol, 2-methyl-2-octanol; (E)-2-hexenol; (E)- and (Z)-3-hexenol; 1-octen-3-ol; a mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol; aliphatic aldehydes and their acetals such as for example hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal-diethylacetal; 1,1-dimethoxy-2,2,5-trimethyl-4-hexene; citronellyl oxyacetaldehyde;

aliphatic ketones and oximes thereof, such as for example 2-heptanone; 2-octanone; 3-octanone; 2-nonanone; 5-methyl-3-heptanone; 5-methyl-3-heptanone oxime; 2,4,4,7-tetramethyl-6-octen-3-one;

aliphatic sulfur-containing compounds, such as for example 3-methylthiohexanol; 3-methylthiohexyl acetate; 3-mercaptohexanol; 3-mercaptohexyl acetate; 3-mercaptohexyl butyrate; 3-acetyltbiohexyl acetate; 1-menthene-8-thiol;

aliphatic nitriles, such as for example 2-nonenenitrile; 2-tridecenenitrile; 2,12-tridecenenitrile; 3,7-dimethyl-2,6-octadienenitrile; 3,7-dimethyl-6-octenenitrile;

aliphatic carboxylic acids other than those included in structure (I) and esters of aliphatic acids, such as for example (E)- and (Z)-3-hexenylformate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexylbutyrate; (E)- and (Z)-3-hexenyl isobutyrate; hexyl crotonate; ethylisovalerate; ethyl-2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyl oxyacetate; methyl-3,7-dimethyl-2,6-octadienoate;

acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerates, pentanoates, hexanoates, crotonates, tiglinates and 3-methyl-2-butenoates thereof;

acyclic terpene aldehydes and ketones, such as, for example, geranial; neral; citronellal; 7-hydroxy-3,7-dimethyloctanal; 7-methoxy-3,7-dimethyloctanal; 2,6,10-trimethyl-9-undecenal; α-sinensal; β-sinensal; geranylacetone; as well as the dimethyl- and diethylacetals of geranial, neral and 7-hydroxy-3,7-dimethyloctanal;

cyclic terpene alcohols, such as, for example, menthol; isopulegol; alpha-terpineol; terpinen-4-ol; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates and 3-methyl-2-butenoates of alpha-terpineol, terpinen-4-ol; methan-8-ol, methan-1-ol, methan-7-ol, borneol, isoborneol, linalool oxide, nopol, cedrol, ambrinol, vetiverol and guaiol; cyclic terpene aldehydes and ketones, such as, for example, menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alphadamascone; beta-damascone; beta-danascenone; deltadamascone; gamma-damascone; 1-(2,4,4-trimethyl-2-cyclohexen-1-yl)-2-buten-1-one; 1,3,4,6,7,8a-hexahydrol; 1,1,5,5-tetramethyl-2H-2,4a-methanonaphthalen-8(5H)-one; nootkatone; dihydronootkatone; acetylated cedarwood oil (cedryl methyl ketone);

cyclic alcohols, such as, for example, 4-tert.-butylcyclohexanal; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

cycloaliphatic alcohols, such as, for example, alpha-3,3-trimethylcyclo-hexyl-methanol; 2-methyl-4-(2,2,3-trimethyl-3-cyclopent-1-yl)-butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)-pentan-3-ol; 1-(2,2,6-trimethylcyclohexyl)-hexan-3-ol;

cyclic and cycloaliphatic ethers, such as, for example, cineole; cedryl methyl ether; cyclododecyl methyl ether; (ethoxymethoxy)-cyclododecane; alpha-cedrene epoxide; 3a,6,6,9a-tetramethyldodecahydronaphtho[2,1-b]furan; 3a-ethyl-6,6,9a-trimethyl-dodecahydronaphtho[2,1-b]furan; 1,5,9-trimethyl-13-oxabicyclo[10.1.0]-trideca-4,8-diene; rose oxide; 2-(2,4-dimethyl-3-cyclohexen-1-yl)-5-methyl-5-(1-methyl-propyl)-1,3-dioxan;

cyclic ketones, such as, for example, 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-lone; 6,7-dihydro-1,1,2,3,3-pentamethyl-4(5H)-indanone; 5-cyclohexadecen-1-one; 8-cyclohexadecen-1-one; 9-cycloheptadecen-1-one; cyclopentadecanone; cycloaliphatic aldehydes, such as, for example, 2,4-dimethyl-3-cyclohexene carbaldehyde; 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

cycloaliphatic ketones, such as, for example, 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphtalenyl methyl ketone; methyl-2,6,10-trimethyl-2,5,9-cyclododecatrienyl ketone; tert.-butyl-(2,4-dimethyl-3-cyclohexen-1-yl)-ketone;

esters of cyclic alcohols, such as, for example, 2-tert.butylcyclohexyl acetate; 4-tert.-butylcyclohexyl acetate; 2-tert.-pentylcyclohexyl acetate; 4-tert.-pentylcyclohexyl acetate; decahydro-2-naphthyl acetate; 3-pentyltetrahy-dro-2H-pyran-4-yl acetate; decahydro-2,5,5,8a-tetramethyl-2-naphthyl acetate; 4,7-methano-3a,4,5,6,7,7a-hexa-hydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

esters of cycloaliphatic carboxylic acids, such as, for example, allyl 3-cyclohexyl-propionate; allyl cyclohexyl oxyacetate; methyl dihydrojasmonate; methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

araliphatic ethers, such as for example, 2-phenylethyl methyl ether; 2-phenylethyl isoamyl ether; 2-phenylethyl-1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

aromatic and araliphatic aldehydes, such as, for example, benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylproparral; 2-methyl-3-(4-isopropylphenyl)-propanal; 2-methyl-3-(4-tert.-butylphenyl)propanal; 3-(4-tert.-butyl-phenyl)propanal; cinnamaldehyde; alphabutylcinnamaldehyde; alpha-amylcinnamaldehyde; alphahexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylene-dioxybenzaldehyde; 3,4-dimethoxybenzaldehyde; 2-methyl-3-(4-methoxyphenyl)-propanal; 2-methyl-3-(4-methylendioxyphenyl)-propanal;

aromatic and araliphatic ketones, such as, for example, acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6hexamethyl-5-indanyl methyl ketone; 6-tert.-butyl-1,1,1-dimethyl-4-indanyl methyl ketone; 1-[2,3-dihydro-1,1,2,6-tetramethyl-3-(1-methyl-ethyl)-1H-5-indenyl]ethanone; 5',6',7',8'-tetrahydro-3',5',5',6',8',8'-hexamethyl-2-acetonaphthone;

aromatic and araliphatic carboxylic acids and esters thereof, such as, for example, benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

nitrogen-containing aromatic compounds, such as, for example, 2,4,6-trinitro-1,3-dimethyl-5-tert-butylbenzene; 3,5-dinitro-2,6-dimethyl-4-tert.-butylacetophenone; cinnamonitrile; 5-phenyl-3-methyl-2-pentenonitrile; 5-phenyl-3-methylpentanonitrile; methyl anthranilate; methyN-methylanthranilate; Schiff's bases of methyl anthranilate with 7-hydroxy-3,7-dimethyloctanal, 2-methyl-3-(4-tert.-butylphenyl)-propanal or 2,4-dimethyl-3-cyclohexene carbaldehyde; 6-isopropylquinoline; 6-isobutylquinoline; 6-sec.- butylquinoline; indole; skatole; 2-methoxy-3-isopropyl-pyrazine; 2-isobutyl-3-methoxypyrazine;

phenols, phenyl ethers and phenyl esters, such as, for example, estragole; anethole; eugenol; eugenyl methyl ether; isoeugenol; isoeugenol methyl ether; thymol; carvacrol; diphenyl ether; beta-naphthyl methyl ether; betanaphthyl ethyl ether; beta-naphthyl isobutyl ether; 1,4-dimethoxybenzene; eugenyl acetate; 2-methoxy-4-methylphenol; 2-ethoxy-5-(1-propenyl)-phenol; p-cresyl phenylacetate;

heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran4-one; 2-ethyl-3-hydroxy-4H-pyran-4-one;

lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-1'-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; coumarin; 2,3-dihydrocoumarin; octahydrocoumarin.

In addition, the odor neutralizing compositions according to the present invention can be adsorbed onto a carrier which ensures both the fine distribution of the odor neutralizer ingredients in the product and controlled release thereof during use. Such carriers can be porous inorganic materials such as light sulfate, silica gels, zeolites, gypsums, clays, granulated clays, aerated concrete, etc., or organic materials such as wood and other cellulose-based materials.

The odor neutralizer compositions containing an alicyclic ketone of structure (I) or a substituted cyclohexanone (e.g., a cyclohexanone substituted with $C_1$-$C_5$ branched or unbranched alkyl) and one or more of the aforementioned acids can also be in microencapsulated or spray-dried form or in the form of inclusion complexes or extrusion products and they can be added in these forms to the product (e.g., a textile cleaner, a hard surface cleaner, or a soft surface cleaner) whose odor is to be improved or which is to be perfumed.

The compositions described in this disclosure may be added to a wide variety of consumer products, such as institutional products, personal care products and cosmetics, both perfumed and perfume-free.

Household products which may comprise a composition according to the disclosure include fabric washing powder and washing liquid, detergent, surface cleaner (including hard surface cleaner), air freshener, softener, bleach, fabric refresher and room spray, disinfection products, scourer and cat litter. The list of household products is given by way of illustration and is not to be regarded as being in any way limiting.

Personal care products and cosmetics which may comprise a composition according to the disclosure include lotions, e.g. after-shave lotion, shampoo, conditioner, styling spray, mousse, gel, hair wipe, hair spray, hair pomade, bath and shower gel, bath salt, hygiene products, deodorant, antiperspirant, breath-freshening sprays, breath-freshening chewing gum, mouthwashes, lozenges and mints, vanishing cream, depilatory, and talcum powder. The list of personal care products and cosmetics is given by way of illustration and is not to be regarded as being in any way limiting.

Typically, the products using the composition described in this disclosure comprise from about 0.0001% to about 60% by weight, preferably about 0.001% to about 20% by weight, of one or more alicyclic ketones of structure (I) or a substituted cyclohexanone (e.g., a cyclohexanone substituted with $C_1$-$C_5$ branched or unbranched alkyl) and at least one of the aforementioned acids based on the product. The effective amount depends upon the type of product into which the combination is admixed.

For example, if used in a fabric refresher the combination may be added to a fragrance composition at around 10% by weight which is then added to the product at around 0.1%-1% by weight; i.e. the fabric refresher comprises about 0.01%-0.1% by weight of the composition as hereinabove described. Or, in a liquid electrical air freshener composition, the combination may be added at as much as 50% by weight based on the air freshener composition.

Accordingly, the present disclosure refers in a further aspect to a consumer product comprising an effective malodor-counteracting amount of a composition comprising one or more of the alicyclic ketones of structure (I) or a substituted cyclohexanone (e.g., a cyclohexanone substituted with $C_1$-$C_5$ branched or unbranched alkyl) and one or more of the aforementioned acids.

Other aspects of the disclosure include methods of removing malodor from the air or from hard or soft surfaces (e.g., textile surfaces), comprising contacting the source of said malodor with an effective amount of a composition comprising one or more of the alicyclic ketones of structure (I) or a substituted cyclohexanone (e.g., a cyclohexanone substituted with $C_1$-$C_5$ branched or unbranched alkyl) and one or more of the aforementioned acids as hereinabove described. The methods can be, for example, spraying the ambient air surrounding the source of the malodors, or spraying an aerosol formulation directly onto the source of the malodor.

In a further aspect, the disclosure features a method of enhancing the malodor reduction properties of a consumer product, such as household products, and personal care products, comprising admixing to the product effective amounts of one or more of the alicyclic ketones of structure (I) or a substituted cyclohexanone (e.g., a cyclohexanone substituted with $C_1$-$C_5$ branched or unbranched alkyl) and one or more of the aforementioned acids.

Testing

Example 1

A malodor evaluation panel of 14 persons was assembled and asked to evaluate the odor neutralizing effectiveness of citric acid and 4-tert-pentylcyclohexanone and certain ionones and irones within the scope of structure (I) separately and in combination. The source of the malodor tested was cat urine.

Swatches of 100% untreated cotton fabric were cut into 15 cm (6-inch) squares and were placed on weighing boats. 1.0 grams of cat urine was pipetted onto each of the swatches. A period of three minutes was allowed for the urine to be absorbed by the fabric.

Onto each swatch, 3.0 grams of a composition was sprayed. As a control, 3.0 grams of water was sprayed on certain swatches.

Each swatch was placed in the middle of a two by two foot (61×61 cm) cubicle and all doors were closed. Actual testing began after thirty minutes.

Each member of the panel was asked to sniff the malodor control first and was notified that the control has a rating of 7—indicating very strong malodor. They were then asked to proceed to sniff the other samples and provide a rating for malodor remaining. Thus, the remaining malodor was evaluated on a sliding scale, with 1 being very weak malodor. The panelists were instructed to ignore any fragrance that they may detect and rate only the malodor.

For the spray compositions containing alicyclic ketone alone and citric acid alone, each spray composition consisted of:
  Test substance—1%
  Neodol 91-8—1%
  Fabric spray base—98%

For the spray compositions containing both an alicyclic ketone and citric acid, each spray composition consisted of:
  Alicyclic ketone—1%
  Acid—1%
  Neodol 91-8—3%
  Fabric spray base—95.0%

Neodol 91-8 is a $C_9$-$C_{11}$ alcohol with an average of approximately 8 moles of ethylene oxide per mole of alcohol. The fabric spray base was an aqueous solution containing 75% distilled water, 20% ethanol, and 5% of non-ionic surfactant.

The results are shown in Table 1. Each panelist tested citric acid, all of the alicyclic ketones, and the combination. The scores reported are therefore the average of 14 replications.

The ionones and irones tested were racemic mixtures of their respective α, β, and γ-isomers. The table sets forth what is believed to be the dominant isomer. Apparent duplications (Tests 5, 6 and 8; Tests 10 and 11) are tests on substances obtained from different sources, and have different mixtures of isomers.

Example 2

A malodor evaluation panel of 14 persons was assembled and asked to evaluate the odor neutralizing effectiveness of citric acid, 4-tert-pentylcyclohexanone, and methyl α-ionone, either alone or in combination. The source of the malodor tested was cigarette smoke.

Swatches of 100% untreated cotton fabric were cut into 15 cm (6-inch) squares and were placed in large plastic containers. Two cigarettes were smoked up inside the plastic containers containing the swatches with closed lids. The environment inside each closed container was allowed to equilibrate for 24 hours.

Onto each swatch, 3.0 grams of a composition was sprayed. As a control, 3.0 grams of water was sprayed on certain swatches.

Each swatch was placed in the middle of a two by two foot (61×61 cm) cubicle and all doors were closed. Actual testing began after thirty minutes.

Each member of the panel was asked to sniff the malodor control first and was notified that the control has a rating of 7—indicating very strong malodor. They were then asked to proceed to sniff the other samples and provide a rating for malodor remaining. Thus, the remaining malodor was evaluated on a sliding scale, with 1 being very weak malodor. The

TABLE 1

| Test No. | Alicyclic ketone | Molecular weight | Score alone 1% | Score of combination 1% + 1% | score of citric acid 1% | (score of ketone) − (score of combination) | (score of citric acid) − (score of combination) |
|---|---|---|---|---|---|---|---|
| 1. | 4-tert-pentylcyclohexanone | 168.2 | 3.50 | 2.90 | 3.40 | 0.60 | 0.50 |
| 2. | α-ionone | 192.3 | 4.20 | 3.10 | 3.20 | 1.10 | 0.10 |
| 3. | β-ionone | 192.3 | 3.80 | 3.10 | 4.10 | 0.70 | 1.00 |
| 4. | dihydro-β-ionone | 194.3 | 3.90 | 2.50 | 3.30 | 1.40 | 0.80 |
| 5. | methyl α-ionone | 206.3 | 3.20 | 2.30 | 4.20 | 0.90 | 1.90 |
| 6. | methyl α-ionone | 206.3 | 3.40 | 3.40 | 4.00 | 0.00 | 0.60 |
| 7. | methyl β-ionone | 206.3 | 3.50 | 3.40 | 4.30 | 0.10 | 0.90 |
| 8. | methyl α-ionone | 206.3 | 2.80 | 2.80 | 4.50 | 0.00 | 1.70 |
| 9. | α-irone | 206.3 | 3.90 | 3.70 | 3.70 | 0.20 | 0.00 |
| 10. | methyl α-ionone | 206.3 | 3.20 | 2.40 | 4.10 | 0.80 | 1.70 |
| 11. | methyl α-ionone | 206.3 | 3.00 | 2.00 | 3.50 | 1.00 | 1.50 |

Following the procedure of Example 1, the odor neutralizing effectiveness of undecylenic acid and two ionones, separately and in combination, was evaluated by a malodor evaluation panel.

The results are shown in Table 2. The ionones tested were mixtures of α, β and γ isomers; the table sets for the dominant isomer.

panelists were instructed to ignore any fragrance that they may detect and rate only the malodor.

For the spray compositions containing citric acid, 4-tert-pentylcyclohexanone, or methyl α-ionone alone, each spray composition (having a total weight of 20.00 g) consisted of:
  Test substance—1% (0.20 g)
  Neodol 91-8—1% (0.20 g)
  Fabric spray base—98% (19.60 g)

TABLE 2

| Test No. | Alicyclic ketone | Molecular weight | Score alone 1% | Score of combination 1% + 1% | score of undecylenic acid 1% | (score of ketone) − (score of combination) | (score of undecylenic acid) − (score of combination) |
|---|---|---|---|---|---|---|---|
| 12. | methyl β-ionone | 206.3 | 2.40 | 2.10 | 3.50 | 0.30 | 1.40 |
| 13. | methyl β-ionone | 206.3 | 3.00 | 2.90 | 3.20 | 0.10 | 0.30 |

For the spray compositions containing both citric acid and 4-tert-pentylcyclohexanone or methyl α-ionone, each spray composition (having a total weight of 20.00 g) consisted of:
Alicyclic ketone—1% (0.20 g)
Acid—1% (0.20 g)
Neodol 91-8—3% (0.60 g)
Fabric spray base—95.0% (19.00 g)

Neodol 91-8 and the fabric spray base were the same as those described in Example 1.

The results are shown in Table 3. Each panelist tested citric acid, 4-tert-pentylcyclohexanone, methyl α-ionone, and their combinations. The scores reported are therefore the average of 14 replications.

TABLE 3

| Name | Molecular Weight (g/mol) | Score of Ketone Alone @ 1% | Score of Combination @ 1% + 1% | Score of Citric Acid @ 1% | (Score of Ketone) − (Score of Combination) | (Score of Acid) − (Score of Combination) |
|---|---|---|---|---|---|---|
| 4-tert-pentylcyclohexanone | 168.2 | 3.40 | 3.10 | 3.90 | 0.30 | 0.80 |
| methyl α-ionone | 206.32 | 4.20 | 3.70 | 4.80 | 0.50 | 1.10 |

Following the procedure described above, spraying compositions containing undecylenic acid and a mixture of isomers of methyl α-ionone, either alone or in combination, were evaluated for their effectiveness in neutralizing malodor caused by cigarette smoke by the malodor evaluation panel. The results are summarized in Table 4, in which the scores reported are the average of 14 replications.

TABLE 4

| Name | Molecular Weight (g/mol) | Score of Ketone Alone @ 1% | Score of Combination @ 1% + 1% | Score of Undecylenic Acid @ 1% | (Score of Ketone) − (Score of Combination) | (Score of Acid) − (Score of Combination) |
|---|---|---|---|---|---|---|
| methyl α-ionone (mixture of isomers) | 206.3 | 2.90 | 2.80 | 4.20 | 0.10 | 1.40 |

Example 3

A malodor evaluation panel of 14 persons was assembled and asked to evaluate the odor neutralizing effectiveness of citric acid and dihydro-β-ionone, either alone or in combination. The source of the malodor tested was synthetic bathroom malodor.

Swatches of 100% untreated cotton fabric were cut into 15 cm (6-inch) squares and were placed on weighing boats. 0.5 grams of synthetic bathroom malodor was pipetted onto each of the swatches. A period of three minutes was allowed for the malodor to be absorbed by the fabric.

Onto each swatch, 3.0 grams of a composition was sprayed. As a control, 3.0 grams of water was sprayed on certain swatches.

Each swatch was placed in the middle of a two by two foot (61×61 cm) cubicle and all doors were closed. Actual testing began after thirty minutes.

Each member of the panel was asked to sniff the malodor control first and was notified that the control has a rating of 7—indicating very strong malodor. They were then asked to proceed to sniff the other samples and provide a rating for malodor remaining. Thus, the remaining malodor was evaluated on a sliding scale, with 1 being very weak malodor. The panelists were instructed to ignore any fragrance that they may detect and rate only the malodor.

For the spray compositions containing citric acid or dihydro-β-ionone alone, each spray composition (having a total weight of 20.00 g) consisted of:
Test substance—1% (0.20 g)
Neodol 91-8—1% (0.20 g)
Fabric spray base—98% (19.60 g)

For the spray composition containing both citric acid and dihydro-β-ionone, the spray composition (having a total weight of 20.00 g) consisted of:
Alicyclic ketone—1% (0.20 g)
Acid—1% (0.20 g)
Neodol 91-8—3% (0.60 g)
Fabric spray base—95.0% (19.00 g)

Neodol 91-8 and the fabric spray base were the same as those described in Example 1.

The results are shown in Table 5. Each panelist tested citric acid, dihydro-β-ionone, and their combinations. The scores reported are therefore the average of 14 replications.

TABLE 5

| Ionone Name | Molecular Weight (g/mol) | Score of Ketone Alone @ 1% | Score of Combination @ 1% + 1% | Score of Citric Acid @ 1% | (Score of Ketone) − (Score of Combination) | (Score of Acid) − (Score of Combination) |
|---|---|---|---|---|---|---|
| dihydro-β-ionone | 194.3 | 3.70 | 3.60 | 5.00 | 0.10 | 1.40 |

Following the procedure described above, compositions containing undecylenic acid, 2-tert-butylcyclohexanone, β-ionone, 1-(2,6,6-trimethyl-2-cyclohexen-1-yl)pent-1-en-3-one, and a mixture of methyl α-ionone, either alone or in combination, were evaluated for their effectiveness in neutralizing synthetic bathroom malodor by the malodor evaluation panel. The results are summarized in Table 6, in which the scores reported are the average of 14 replications.

TABLE 6

| Ionone Name | Molecular Weight (g/mol) | Score of Ketone Alone @ 1% | Score of Combination @ 1% + 1% | Score of Undecylenic Acid @ 1% | (Score of Ketone) – (Score of Combination) | (Score of Acid) – (Score of Combination) |
|---|---|---|---|---|---|---|
| 2-tert-butylcyclohexanone | 154 | 4.50 | 4.10 | 4.30 | 0.40 | 0.20 |
| β-ionone | 192.3 | 4.60 | 3.30 | 5.10 | 1.30 | 1.80 |
| 1-(2,6,6-trimethyl-2-cyclohexen-1-yl)pent-1-en-3-one | 206.3 | 2.80 | 2.70 | 5.20 | 0.10 | 2.50 |
| methyl α-ionone (mixture of isomers) | 206.3 | 3.80 | 3.40 | 5.00 | 0.40 | 1.60 |

What is claimed is:

1. A malodor neutralizing composition, comprising:
   (1) a cyclohexanone substituted with $C_1$-$C_5$ branched or unbranched alkyl or an unsaturated alicyclic ketone of the formula

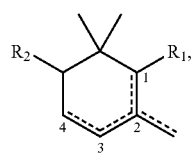

(I)

wherein
   the ring contains 1 double bond at position 1, position 2 (endocyclic) or position 2 (exocyclic) or contains 2 conjugated double bonds at positions 1 and 3,
   $R_1$ is a branched or unbranched $C_3$-$C_5$ alkyl containing a carbonyl or a branched or unbranched $C_3$-$C_5$ alkenyl containing a carbonyl, and
   $R_2$ is hydrogen or methyl; and
   (2) citric acid or undecylenic acid;
   wherein the composition is free of a nitrile and the amount of ingredient (2) is 10-50% by weight of the total amount of ingredients (1) and (2).

2. The composition of claim 1, wherein ingredient (1) is an unsaturated alicyclic ketone of structure (I).

3. The composition of claim 2, wherein $R_1$ is alkyl or alkylene having 4 or 5 carbon atoms and the carbonyl group is in the 1' position or 3' position relative to the ring.

4. The composition of claim 3, wherein $R_1$ is alkylene having 5 carbon atoms.

5. The composition of claim 2, wherein the unsaturated alicyclic ketone has the structure

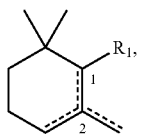

(IV)

in which, in $R_1$, the carbonyl group is in the 3' position relative to the ring.

6. The composition of claim 5, wherein the unsaturated alicyclic ketone is

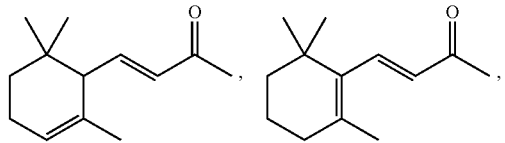

-continued

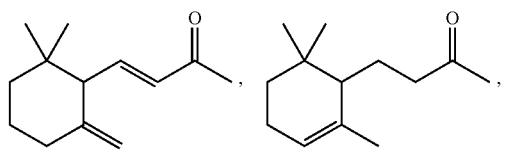

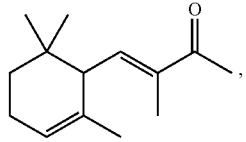

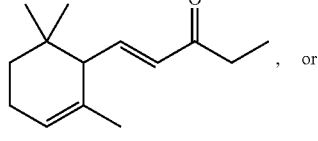, or

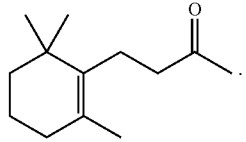

7. The composition of claim 2, wherein the unsaturated alicyclic ketone has the structure

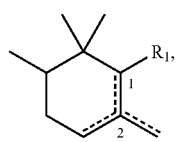

(V)

in which, in $R_1$, the carbonyl group is in the 3' position relative to the ring.

8. The composition of claim 7, wherein the unsaturated alicyclic ketone is

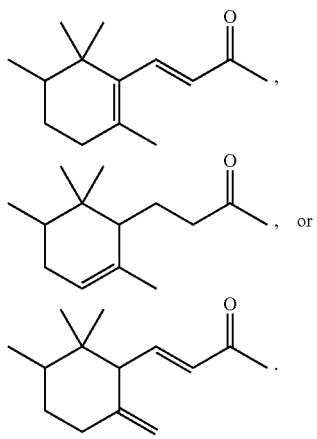

9. The composition of claim 2, wherein the unsaturated alicyclic ketone has the structure

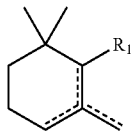
(VI)

in which, in $R_1$, the carbonyl group is in the 1' position relative to the ring.

10. The composition of claim 9, wherein the unsaturated alicyclic ketone is

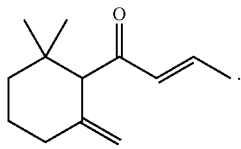

11. The composition of claim 2, wherein the unsaturated alicyclic ketone has the structure

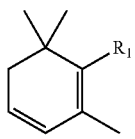
(VII)

in which, in $R_1$, the carbonyl group is in the 1' position relative to the ring.

12. The composition of claim 11, wherein the unsaturated alicyclic ketone is

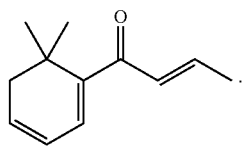

13. The composition of claim 1, wherein the ingredient (1) is a cyclohexanone substituted with $C_1$-05 branched or unbranched alkyl.

14. The composition of claim 13, wherein the cyclohexanone is

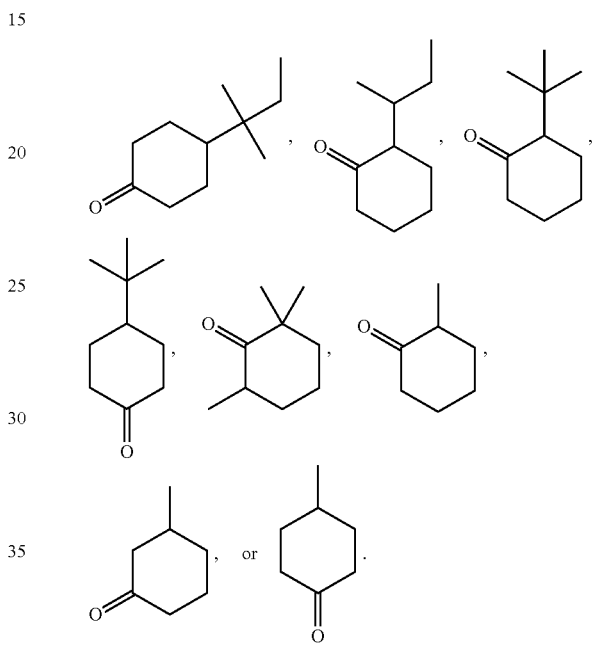

15. The composition of claim 1, wherein ingredient (2) is citric acid.

16. The composition of claim 1, wherein ingredient (2) is undecylenic acid.

17. A product, comprising:
   the malodor neutralizing composition of claim 1;
   wherein the product is a perfumed product, a household product, or a personal care product.

18. A method for reducing malodor, comprising:
   contacting a source of the malodor with an effective amount of the composition of claim 1.

19. A method for reducing malodors emanating from a household or personal care product, comprising:
   admixing to the product the malodor neutralizing composition of claim 1.

\* \* \* \* \*

UNITED STATES PATENT AND TRADEMARK OFFICE
CERTIFICATE OF CORRECTION

PATENT NO. : 9,114,180 B2  Page 1 of 1
APPLICATION NO. : 13/829487
DATED : August 25, 2015
INVENTOR(S) : Stephen V. Dente et al.

It is certified that error appears in the above-identified patent and that said Letters Patent is hereby corrected as shown below:

In the Specification

Column 5, Lines 26-35, after, "Damascenone itself has the structure:" delete

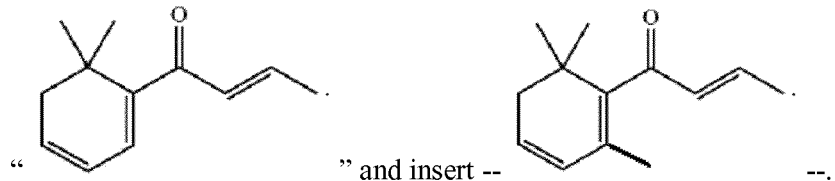

" and insert -- -- .

In the Claims

Column 20, Lines 1-7, Claim 12, delete "

" and insert -- -- .

Column 20, Line 10, Claim 13, delete "$C_1$-05" and insert -- $C_1$-$C_5$ --.

Signed and Sealed this
Twelfth Day of January, 2016

Michelle K. Lee
*Director of the United States Patent and Trademark Office*